US008710843B2

(12) United States Patent
Carlone et al.

(10) Patent No.: US 8,710,843 B2
(45) Date of Patent: Apr. 29, 2014

(54) MAGNETIC RESONANCE IMAGING APPARATUS FOR USE WITH RADIOTHERAPY

(75) Inventors: Marco Carlo Carlone, Toronto (CA); David A. Jaffray, Etobicoke (CA)

(73) Assignee: University Health Network, Toronto (CA)

( * ) Notice: Subject to any disclaimer, the term of this patent is extended or adjusted under 35 U.S.C. 154(b) by 546 days.

(21) Appl. No.: 13/095,281

(22) Filed: Apr. 27, 2011

(65) Prior Publication Data

US 2011/0260729 A1    Oct. 27, 2011

Related U.S. Application Data

(60) Provisional application No. 61/328,245, filed on Apr. 27, 2010.

(51) Int. Cl.
 *G01R 33/32* (2006.01)
(52) U.S. Cl.
 USPC ............ 324/318; 324/307; 324/309; 600/436
(58) Field of Classification Search
 USPC ..................... 324/307, 309, 318; 600/436
 See application file for complete search history.

(56) References Cited

U.S. PATENT DOCUMENTS

| 4,318,043 A * | 3/1982 | Crooks et al. ................. 324/309 |
| 5,600,245 A * | 2/1997 | Yamamoto et al. ............ 324/318 |
| 6,366,798 B2 | 4/2002 | Green |
| 2004/0085170 A1 | 5/2004 | Kruip et al. |
| 2005/0197564 A1 | 9/2005 | Dempsey |
| 2006/0125475 A1 * | 6/2006 | Sodickson et al. ............ 324/300 |
| 2008/0204012 A1 * | 8/2008 | Krueger et al. ............... 324/300 |
| 2008/0208036 A1 | 8/2008 | Amies et al. |
| 2009/0149735 A1 | 6/2009 | Fallone et al. |
| 2010/0013418 A1 * | 1/2010 | Kruip et al. .................. 315/501 |

FOREIGN PATENT DOCUMENTS

| WO | 2004024235 A1 | 3/2004 |
| WO | 2006136865 A1 | 12/2006 |
| WO | 2009113069 A1 | 9/2009 |
| WO | 2009155700 A1 | 12/2009 |

OTHER PUBLICATIONS

Hammer B. E., Christensen, N. L., King, W., Conroy, M. J., Pogue, N. Integration of a 6MeV Electron Beam LINAC with a 1.5 T MRI Scanner. In: Proc Intl Soc Mag Reson Med 2004; 2004. p. 972.

(Continued)

*Primary Examiner* — Melissa Koval
*Assistant Examiner* — Rishi Patel
(74) *Attorney, Agent, or Firm* — Norton Rose Fulbright Canada LLP

(57) ABSTRACT

A magnetic resonance imaging (MRI) apparatus suitable for radiotherapy. The apparatus includes two sets of coil pairs, each coil pair forming a Maxwell-like coil. The two sets of coil pairs share a common transverse plane, have opposing polarities, and define a common plane of symmetry and an imaging area. The two sets generate a substantially homogenous electromagnetic field in a first transverse direction in the imaging area and peripheral electromagnetic fields in a direction opposite to the first transverse direction in a peripheral area. The apparatus also includes at least one focusing magnet positioned in the peripheral areas to generate a focusing electromagnetic field in a focusing area, in a direction substantially the same as the first transverse direction. At least a portion of the peripheral electromagnetic fields is maintained in a defocusing area between the focusing area and the imaging area.

20 Claims, 15 Drawing Sheets

(56) References Cited

OTHER PUBLICATIONS

Fallone B. G., Murray B., Rathee S., et al. "First MR images obtained during megavoltage photon irradiation from a prototype integrated linac-MR system," Med Phys, 36, 2009, 2084-8.

Raaymakers B. W., Lagendijk J. J., Overweg J., et al. "Integrating a 1.5 T MRI scanner with a 6 MV accelerator: proof of concept," Phys Med Biol, 54, 2009, N229-37.

Bielajew A. F. "The effect of strong longitudinal magnetic fields on dose deposition from electron and photon beams," Med Phys, 20, 1993, 1171-9.

Kirkby C., Stanescu T., Rathee S., Carlone M., Murray B., Fallone B. G. "Patient dosimetry for hybrid MRI-radiotherapy systems," Med Phys, 35, 2008, 1019-27.

Nath R., Schulz R. J. "Modification of electron-beam dose distributions by transverse magnetic fields," Med Phys, 5, 1978, 226-30.

Paliwal B. R., Wiley A. L., Jr., Wessels B. W., Choi M. C. "Magnetic field modification of electron-beam dose distributions in inhomogeneous media," Med Phys, 5, 1978, 404-8.

Raaijmakers A. J., Hardemark B., Raaymakers B. W., Raaijmakers C. P., Lagendijk J. J. "Dose optimization for the MRI-accelerator: IMRT in the presence of a magnetic field," Phys Med Biol, 52, 2007, 7045-54.

Raaijmakers A. J., Raaymakers B. W., Lagendijk J. J. "Integrating a MRI scanner with a 6 MV radiotherapy accelerator: dose increase at tissue-air interfaces in a lateral magnetic field due to returning electrons," Phys Med Biol, 50, 2005, 1363-76.

Raaijmakers A. J., Raaymakers B. W., Lagendijk J. J. "Experimental verification of magnetic field dose effects for the MRI-accelerator," Phys Med Biol, 52, 2007, 4283-91.

Raaijmakers A. J., Raaymakers B. W., Lagendijk J. J. "Magnetic-field-induced dose effects in MR-guided radiotherapy systems: dependence on the magnetic field strength," Phys Med Biol, 53, 2008, 909-23.

Raaijmakers A. J., Raaymakers B. W., Van Der Meer S., Lagendijk J. J. "Integrating a MRI scanner with a 6 MV radiotherapy accelerator: impact of the surface orientation on the entrance and exit dose due to the transverse magnetic field," Phys Med Biol, 52, 2007, 929-39.

Raaymakers B. W., Raaijmakers A. J., Kotte A. N., Jette D., Lagendijk J. J. "Integrating a MRI scanner with a 6 MV radiotherapy accelerator: dose deposition in a transverse magnetic field," Phys Med Biol, 49, 2004, 4109-18.

Weinhous M. S., Nath R., Schulz R. J. "Enhancement of electron beam dose distributions by longitudinal magnetic fields: Monte Carlo simulations and magnet system optimization," Med Phys, 12, 1985, 598-603.

Whitmire D. P., Bernard D. L., Peterson M. D., Purdy J. A. "Magnetic enhancement of electron dose distribution in a phantom," Med Phys, 4, 1977, 127-31.

Burke B., Lamey M., Rathee S., Murray B., Fallone B. G. "Radio frequency noise from clinical linear accelerators," Phys Med Biol, 54, 2009, 2483-92.

Lamey M., Rathee, S., Johnson, L., Carlone, M., Blosser, E., Fallone, B.G. Radio frequency noise from the modulator of a linac. In: IEEE Transactions on Electromagnetic Compatibility; 2010.

Lamey M., Burke B., Blosser E., Rathee S., De Zanche N., Fallone B. G. "Radio frequency shielding for a linac-MRI system," Phys Med Biol, 55, 2009, 995-1006.

Lamey M., Yun J., Burke B., Rathee S., Fallone B. G. "Radio frequency noise from an MLC: a feasibility study of the use of an MLC for linac-MR systems," Phys Med Biol, 55, 2009, 981-94.

Schenck J. F., Jolesz F. A., Roemer P. B., et al. "Superconducting open-configuration MR imaging system for image-guided therapy," Radiology, 195, 1995, 805-14.

Septier A. L. Focusing of Charged Particles: Academic Press; 1967.

Septier A. L. Applied charged particle optics. New York: Academic Press; 1980.

Humphries S. Principles of charged particle acceleration. New York: J. Wiley; 1986.

Karzmark C. J., Nunan C. S., Tanabe E. Medical electron accelerators. New York: McGraw-Hill, Inc., Health Professions Division; 1993.

Litzenberg D. W., Fraass B. A., McShan D. L., et al. "An apparatus for applying strong longitudinal magnetic fields to clinical photon and electron beams," Phys Med Biol, 46, 2001, N105-15.

Romeo F., Hoult D. I. "Magnet field profiling: analysis and correcting coil design," Magn Reson Med, 1, 1984, 44-65.

Chen Y., Bielajew A. F., Litzenberg D. W., Moran J. M., Becchetti F. D. "Magnetic confinement of electron and photon radiotherapy dose: a Monte Carlo simulation with a nonuniform longitudinal magnetic field," Med Phys, 32, 2005, 3810-8.

Kawrakow I., Rogers, D. W. O. . The EGSnrc Code System: Monte Carlo Simulation of Electron and Photon Transport. Ottawa: NRC; 2003. Report No. NRCC Report PIRS-701.

Salvat F., Fernández-Varea, J. M., Acosta, Sempau, J. Penelope: A Code System for Monte Carlo Simulation of Electron and Photon Transport. Issy-les-Moulineaux: OECD Nuclear Energy Agency; 2003.

\* cited by examiner

MAGNETIC RESONANCE IMAGING APPARATUS FOR USE WITH RADIOTHERAPY

CROSS-REFERENCE TO RELATED APPLICATIONS

The present disclosure claims priority from U.S. provisional patent application No. 61/328,245, filed Apr. 27, 2010, the entirety of which is hereby incorporated by reference.

TECHNICAL FIELD

The present disclosure relates generally to a magnetic resonance imaging (MRI) apparatus suitable for use with radiotherapy. In particular, the present disclosure relates to an MRI apparatus for generating electromagnetic fields suitable for use with electron linear accelerators in radiotherapy applications.

BACKGROUND

Image guidance in radiotherapy is an active area of commercial development and research. Systems using megavolt (MV) detectors, kilovolt (kV) X-ray sources and detectors, ultrasound, and radiofrequency emitting fiducials have been described and commercialized. To this end, there has been interest in combining a linear accelerator, used in radiotherapy, with magnetic resonance imaging (MRI) to improve image guidance. MRI offers relatively good soft tissue contrast and can image in any arbitrary plane in the patient, including the beam's-eye view, which may be useful in radiotherapy. The first demonstration of this principle was first described by Hammer and colleagues[1], and more recently two other groups have also demonstrated that a linear accelerator and MRI can co-exist in even closer proximity[2,3].

Some difficulties with integrating MRI with radiotherapy may include the following:

1. The linear accelerator operates by accelerating an electron to high energies before converting this energy to X-rays by smashing the electron into a target and the bremsstrahlung process. The motion of the electron in the linear accelerator is thus affected by a magnetic field, such as that required for MRI, by the Lorentz force, $F=ev \times B$ (where F is the force exerted on a particle, e is the charge of the particle, v is the instantaneous velocity of the particle and B is the strength of the magnetic field), which could prevent or hamper the functionality of the linear accelerator.

2. MRI typically require a relatively high degree of homogeneity in the magnetic field for imaging, which is most easily achieved by constructing the MRI magnet such that it surrounds the patient, and may thus prevent or impede open access to the patient by the linear accelerator.

3. The radiotherapy dose distribution in the patient is affected by the magnetic field in the patient since the electrons scattered by the incident photons are also affected by the magnetic field of the MRI by the Lorentz force $F=ev \times B$[4-15]. This disturbance of the dose distribution can be significant, particularly at higher magnetic fields, and can yield considerable dose differences, especially in regions in the patient where there is a tissue density inhomogeneity. In this case an effect called the "dose return effect[9]" has been described where scattered electrons in a distal lower density medium have a sufficiently large range such that their trajectory can return to a proximal higher density tissue, and deposit an unintended supplemental dose.

4. Other difficulties also exist such as radiofrequency (RF) interference[16-19], however it has been demonstrated that these can effectively be removed or diminished by shielding[2,3].

To overcome the first three problems, several designs of an integrated MRI and linear accelerator have been proposed, and several patents and patent applications have been published[20-25]. With the exception of Amies et al[20] and Carlone et al[26], these solutions seek to avoid the first problem listed above by removing the magnetic field from the MRI in the area where the linear accelerator will be located. This may be done by passive or active magnetic shielding of the linear accelerator. This approach may have some difficulties. One difficulty is that the introduction of shielding affects the design of the MRI magnet; the complexity of a magnet that can shield a region for a linear accelerator and still maintain parts-per-million (ppm) homogeneity at the imaging zone is typically higher than typical MRI magnets. Another difficulty is that this method encourages the use of distance to facilitate magnetic isolation, which may be a drawback since a compact design may be useful to facilitate the use of this technology in a hospital setting, where space is often restricted. Another difficulty is that this method may push the fringe field of the MRI magnet outward since a low field zone is generated near the centre of the MRI. This extension of the fringe field can be a serious problem, and can affect the MRI facility specification.

The second and third problems listed above, generally, are not completely resolved by the conventional or suggested methods described above. The conventional approaches used to overcome the second problem (i.e., need for direct view of the patient within the MRI by the linear accelerator) include:

1. To use an open magnet configuration and rotate the magnet about the patient[2,22,23];

2. To employ a cylindrical MRI magnet that has been separated by a small gap, and irradiate through the gap[25];

3. To use an MRI magnet specifically designed for interventional radiology[21,27]; or 4. To use an MRI magnet that is large enough to accept the entire linear accelerator within its bore[20].

None of the conventional or proposed linear accelerator designs described above overcomes the third problem (i.e., perturbation of the dose distribution in the patient by the magnetic field of the MRI), but some methods have been suggested to minimize this effect, including:

1. To use a low magnetic field such that the effect is small[5], or

2. To employ complex beam geometries to compensate for the perturbed dose distribution[8].

It should be noted that conventional and suggested solutions for MRI guidance of radiotherapy typically does not consider that isolation of the linear accelerator from a magnetic field is not required to maintain functionality of the linear accelerator. Focusing of charged particles by electromagnetic forces is a field of investigation that has been used in areas of ion implantation, ion gun design, high energy particle accelerators, and many others[28,29]. As well, magnetic field focusing of electrons in traveling wave linear accelerators is a component of their design, and these devices would not function without such focusing[30,31]. The principle of such focusing is that the linear accelerator is immersed in a non-uniform magnetic field that is parallel to the direction of motion of the particle travel. Particles that are precisely on the central axis of the magnetic field have no magnetic force exerted upon them, and so they stay aligned with the central axis. Particles that are parallel to the magnetic field, but off-axis (because they were miss-aligned when injected, for instance), will interact with the radial component of the magnetic field causing a circular trajectory about the central axis of the magnetic field, and perpendicular to this axis. Such motion results in a central and focusing force upon the charged particle because of interaction with the axial magnetic field (for example, a complete description is given on p. 126 of Humphreys[30]).

Based on this observation, it may be possible to integrate a linear accelerator into an MRI magnet and maintain functionality of the linear accelerator if its orientation were such that it was parallel to the magnetic field of the MRI, and pointed towards the MRI's isocenter. One way of doing this may be to use a parallel coil configuration, such as the ones used in commercially available open magnets, with the linear accelerator placed in the centre of one of the coils, for example as described in the patent application by Carlone et al[26]. An example of this method is illustrated in FIG. 1.

FIG. 1 shows an example magnet coil 1 and an example linear accelerator 2. In this example the current flow in the magnet coil is shown to be clockwise 3 and produces a magnetic field direction that is downward 5. The electronic motion inside the linear accelerator is downward 4 and parallel to the direction of the magnetic field 5 and so the linear accelerator may function well while in the magnetic field and may not need to be isolated from it. The imaging target 6 may be positioned inside the X-ray field 7, whose direction is also parallel to the direction of the MRI magnetic field.

This arrangement may address problems 1 and 3 listed in the above. Problem one may be overcome since the method does not rely on magnetic shielding for linear accelerator integration into an MRI magnet. Problem 3 may be also overcome because, as described by Bielajew[4], the scattered electrons generated by photon interactions are also focused by the magnetic field, which result in less lateral scatter. The undesirable "electron return effect" as described by Raaijmakers and colleagues[9] may be eliminated for this configuration. However, other problems may arise, as will be described below.

SUMMARY

In some example aspects of the present disclosure, there is provided a magnetic resonance imaging (MRI) apparatus suitable for radiotherapy, the apparatus comprising: two sets of coil pairs, each set having at least one coil pair, each coil pair comprising two individual coils having different polarities, superimposed over each other and sharing a common axis of rotation; the coil pairs in each set of coil pairs sharing a common transverse plane; the two sets of coil pairs sharing the common transverse plane and being parallel to and spaced apart from each other, the two sets of coil pairs having opposing polarities, and defining a common plane of symmetry and an imaging area between the two sets of coil pairs; the two sets of coil pairs being configured to generate a substantially homogenous electromagnetic field in a first transverse direction in the common transverse plane, in the imaging area between the two sets of coil pairs; the two sets of coil pairs also being configured to generate peripheral electromagnetic fields in a second transverse direction opposite to the first transverse direction in a peripheral area outside of the imaging area; and at least one focusing magnet positioned in the peripheral areas, substantially parallel to the first transverse direction, the at least one focusing magnet being configured to generate a focusing electromagnetic field in a focusing area, in a direction substantially the same as the first transverse direction; wherein at least a portion of the peripheral electromagnetic fields is maintained in a defocusing area between the focusing area and the imaging area.

In some examples, the apparatus may be rotatable about the imaging area. In some embodiments, each set of coil pairs may comprise a plurality of coil pairs, wherein the polarity of each coil pair may be individually selectable to dynamically define the plane of symmetry in any one of a plurality of defined orientations and to dynamically change the orientation of the transverse directions of the generated electromagnetic fields, and wherein the at least one focusing magnet may be rotatable about the imaging area to match the changed transverse directions.

In some examples, the apparatus may be configured to accommodate a linear accelerator for radiotherapy in the focusing area, where the linear accelerator may be configured to emit a radiation beam in the direction of the first transverse direction.

In some example aspects, there is also provided a system for magnetic resonance imaging (MRI) suitable for use with radiotherapy, the system comprising: the apparatus described above; and a linear accelerator for radiotherapy, the linear accelerator being positioned to emit a radiation beam into the imaging area, in the direction of the first transverse direction, the linear accelerator also being positioned in the focusing area.

In some examples, where the at least one focusing magnet of the apparatus is rotatable about the imaging area, the linear accelerator may be also rotatable about the imaging area to match the focusing area of the focusing magnet.

BRIEF DESCRIPTION OF THE DRAWINGS

Reference will now be made to the drawings, which show by way of example embodiments of the present disclosure, and in which.

DETAILED DESCRIPTION

Figure 1:
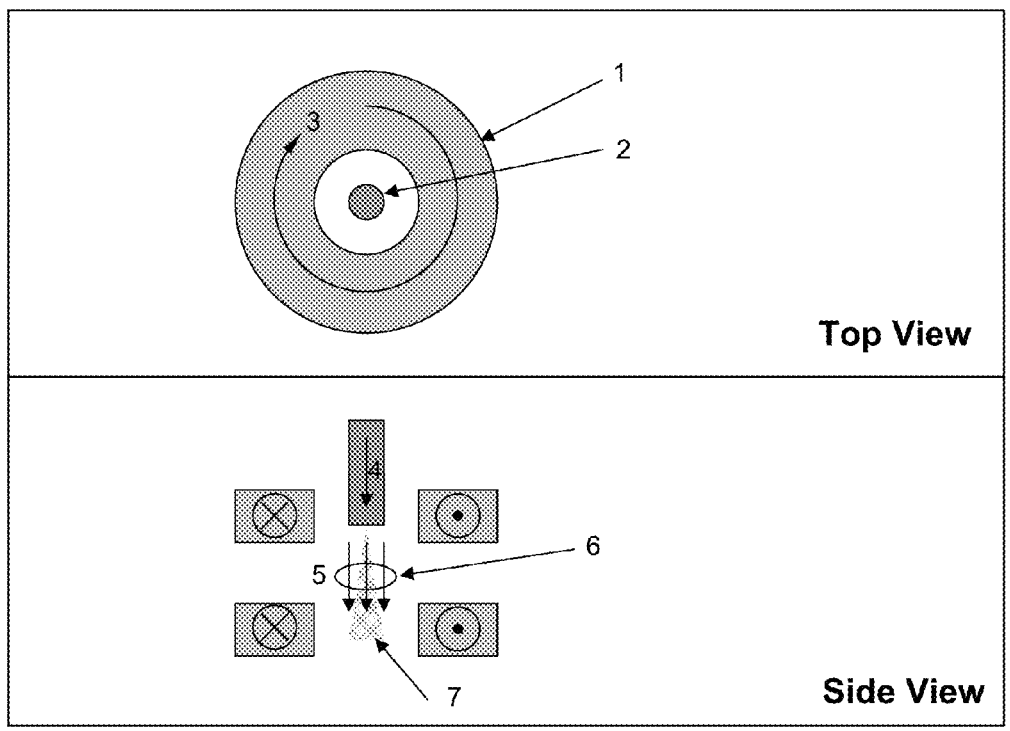
FIG. 1 shows an example prior art MRI coil arrangement.

The configuration of FIG. 1 may introduce a new problem. As described by Litzenburg and colleagues[32], a significant patient surface dose may be created since the electrons set in motion in the linear accelerator collimator and air where the X-ray beam passes may also be focused by the parallel magnetic field. These electrons have relatively high energy, and they may be guided to a region on the patient's surface at the centre of the field by the same mechanism that focuses electron motion in a parallel magnetic field. The measurements made by Litzenburg et al. show that this effect may be significant, and may thus create a clinically unusable photon beam.

The arrangement shown in FIG. 1 may be suitable for radiotherapy if a way can be found to defocus or stop electrons that are scattered by interactions with collimators, jaws or air in between the target and patient. Due to the high energy of these electrons, the use of an electric field would require high voltages, (e.g., in the order of MV) which may be impractical. Another way of doing this would be to introduce a defocusing magnetic field in the region where scattering objects would be located, an example of which is shown in FIG. 2.

Figure 2:
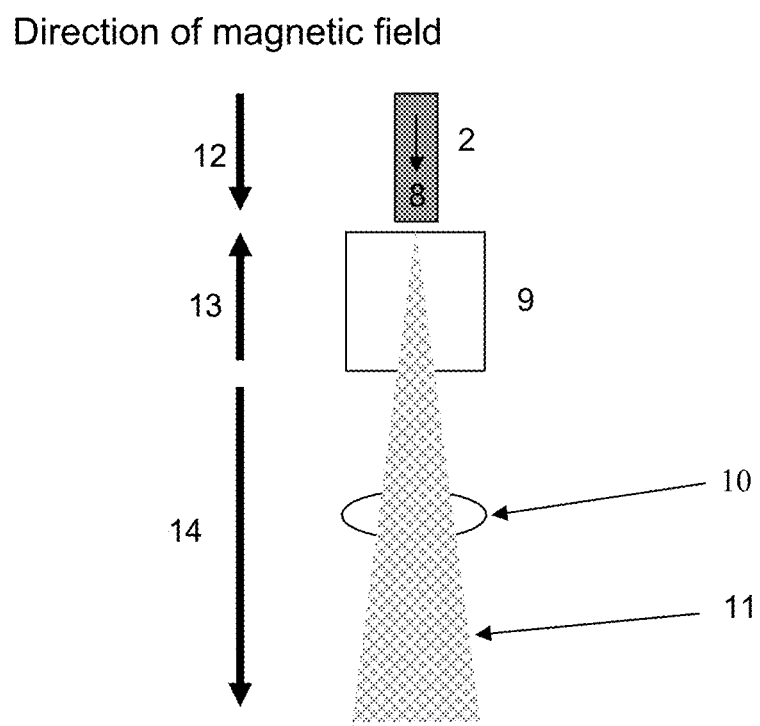
FIG. 2 is a diagram illustrating an example magnetic field.

In the example of FIG. 2, the electron motion 8 within the linear accelerator 2 may be in the same direction as an external magnetic field 12 (e.g., a field produced by an MRI apparatus). In the region 9 where the X-ray beam may be formed and X-ray targets, flattening filters, ion chambers, field defining jaws, multileaf collimators and/or other suitable items may be positioned, the magnetic field 13 may be reversed which may scatter stray electrons produced in this region. In the region where the imaging target 10 may be located, a second magnetic field reversal may produce a magnetic field that may be in the same direction as the X-ray beam 11. The electrons that are scattered from photons incident upon collimators, jaws, ion chambers and/or flattening filters may be subject to a reverse magnetic field, so the action on these scattered particles may be defocusing, which may direct particles away from the central axis, and may reduce or eliminate the surface dose on the imaging target. To produce such a field pattern using conventional solenoid or open magnets (such as the one shown in FIG. 1) may be relatively difficult since these magnets typically produce a unidirectional magnetic field. It may be desirable to address this difficulty.

An example of an MRI apparatus suitable for use with radiotherapy equipment, in particular an electron linear accelerator, is now described. The example apparatus may include Maxwell-like coils. A Maxwell-like coil, in the present disclosure, may refer to a pair of electromagnetic coils having different polarities, superimposed over each other and sharing a common axis of rotation. An axis of rotation may refer to the clockwise or counter-clockwise direction of the coil polarity, rather than actual rotation of the coil. The Maxwell-like coil of the present disclosure may be not necessarily a true Maxwell coil (which has certain defined radii and separation between the coils). The Maxwell-like coil may also be referred to in the present disclosure as a coil pair. The separation between the individual coils of the Maxwell-like coil may be varied and may be unrelated to the radii of the individual coils. The individual coils of the Maxwell-like coil may have equal or unequal radii, and may have any geometry, including, for example, circular, square, D-shaped and banana-shaped, among others. In general, the Maxwell-like coil may be configured to produce an electromagnetic field directed in a transverse plane parallel to and in-between the two individual coils. The transverse plane may be equally distanced from each individual coil (e.g., where the individual coils have equal radii) or may be spaced closer to one of the individual coils (e.g., where the individual coils have unequal radii).

The example apparatus may include two sets of Maxwell-like coils or coil pairs. Each set may include one or more Maxwell-like coil spaced apart and aligned substantially parallel to each other, sharing a common transverse plane, with the same orientation of polarities. Where there are multiple Maxwell-like coils in the set, each Maxwell-like coil may have a different configuration (e.g., different spacing of individual coils from the common transverse plane, different radii of individual coils) provided a common electromagnetic field directed in the common transverse plane is generated.

The two sets of Maxwell-like coils may be aligned substantially parallel to each other, sharing the common transverse plane, and defining an imaging area with a plane of symmetry perpendicular to the common transverse plane. The two sets of Maxwell-like coils may be arranged on either side of the plane of symmetry, with opposing polarities. The two sets of Maxwell-like coils may be symmetrical about the plane of symmetry. The two sets of Maxwell-like coils may be configured to generate a substantially homogenous electromagnetic field in a first transverse direction in the common transverse plane, perpendicular to the plane of symmetry, in the imaging area. The two sets of Maxwell-like coils may further generate peripheral electromagnetic fields in a second transverse direction in the common transverse plane, opposite to the first transverse direction in a peripheral area around the coils, outside of the imaging area. This example arrangement may further include a pair of focusing magnets arranged on opposing sides of the two sets of Maxwell-like coils, symmetrically on either side of the plane of symmetry, substantially parallel to the first transverse direction. The focusing magnets may generate focusing electromagnetic fields in a direction substantially the same as the first transverse direction. It may be suitable to position a linear accelerator in the area of the focusing magnetic field.

This example arrangement may be further described with reference to the figures. A Maxwell coil arrangement is a well-known arrangement where two circular coils that have a common axis of rotation carry currents in opposite directions (i.e., have opposite polarities). If the separation between the coils is the radius times $4/\sqrt{3}$, then the magnetic field is null at the midpoint and the gradient is approximately linear. In the transverse direction, the field goes radially outward or inward, depending on the current directions. A region of magnetic field homogeneity can be generated by placing two sets of coils that have opposing currents in them, e.g., two Maxwell-like coils, in a side by side arrangement. To illustrate how the magnetic fields from these coil configurations can add to form a homogeneous magnetic field region, two sets of example circular coils are shown in FIGS. 3A and 3B.

Figure 3A:
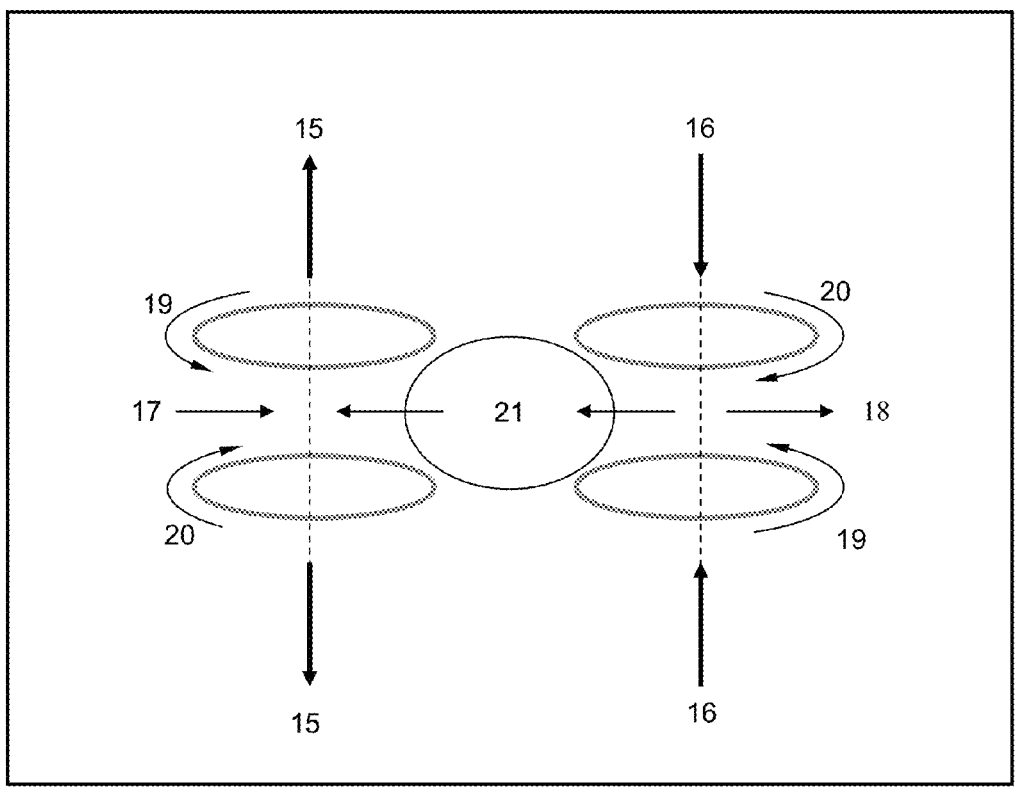
FIG. 3A shows an example coil arrangement suitable for generating the magnetic field of FIG. 2.

FIG. 3A shows an example of two sets of Maxwell-like coils (e.g., true Maxwell coils) that are adjacent to one another, each set having one Maxwell-like coil. In the set on the left of the figure, the top coil has counter clockwise current 19, whereas the bottom coil has clockwise current 20. This produces magnetic field pattern 15 which is directed away from the centre of the coil in the axial direction. In the transverse direction, the magnetic field for this set of coils 17 is pointed towards the centre of the coils. The set of coils in the right of the figure has an opposite configuration. The top coil has clockwise current 20, the bottom coil has counter clockwise current 19, the axial magnetic field 16 is directed towards the centre of the coils and the transverse magnetic field 18 is directed away from the centre of the coils. The region 21 in between the coils has a transverse magnetic field from each coil that is in the same direction, and can be made to have a relatively homogeneous magnetic field that may be suitable for MRI imaging using conventional techniques, for example by proper selection of the coil arrangement. FIG. 3B shows the full magnetic field pattern on the transverse plane for the two Maxwell-like coils.

Figure 3B:
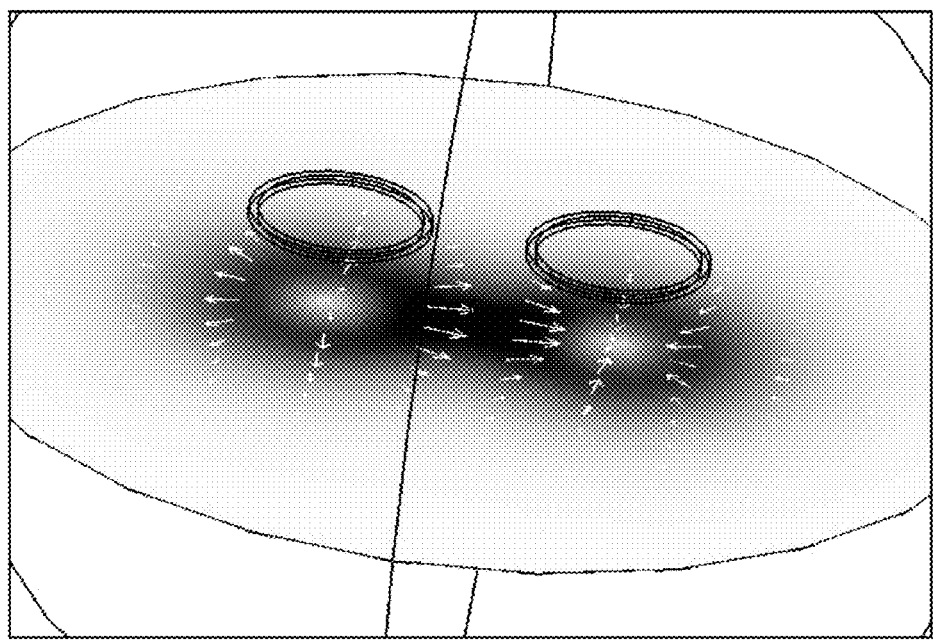
FIG. 3B shows an example magnetic field generated by the coil arrangement of FIG. 3A.

For a current arrangement similar to that shown in FIGS. 3A and 3B to produce a homogeneous region of magnetic field in an imaging area between the two sets of Maxwell-like coils, non-circular arrangements of Maxwell-like may be needed in general. For example, D-shaped coils or banana-shaped Maxwell-like coils may be naturally suited to producing a homogeneous magnetic field on a spherical surface, however those skilled in the art will recognize that many different types of coil configurations can be utilized to the generate the desired homogeneous and transverse magnetic field. The magnet configuration used in an example of the present disclosure may include a set of Maxwell-like coils that may be circular and thus simpler to model and illustrate principles with, however many other basic geometries may be used to generate a relatively homogeneous magnetic field from Maxwell-like coils.

Figure 4:
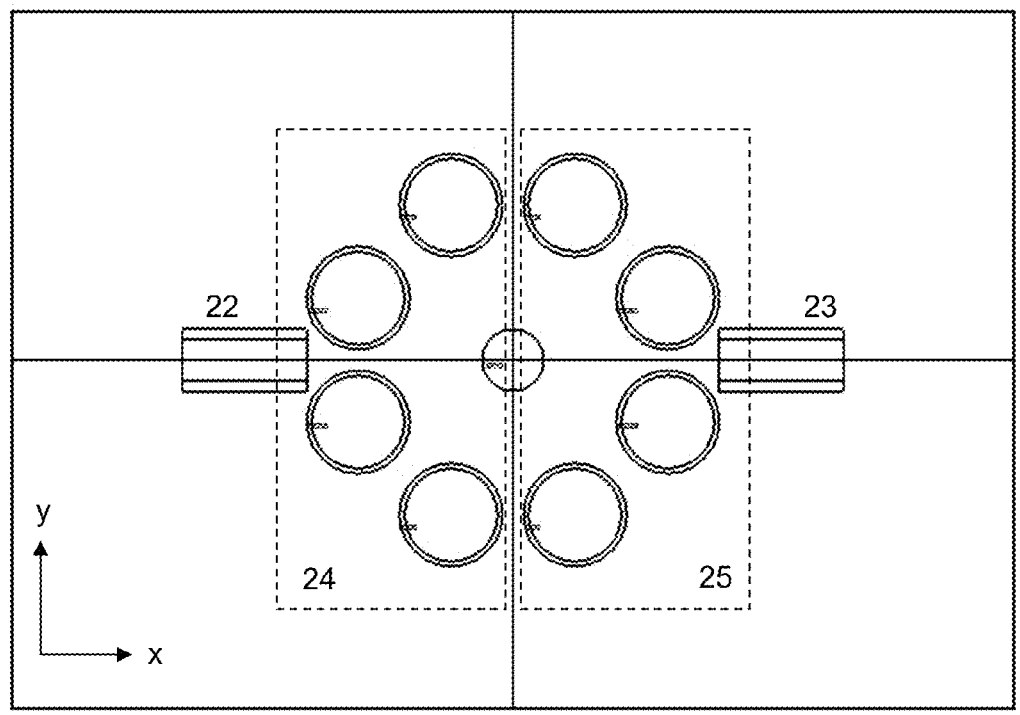
FIG. 4 shows a view of the transverse plane of an example MRI arrangement suitable for use with radiotherapy.
Figure 5:
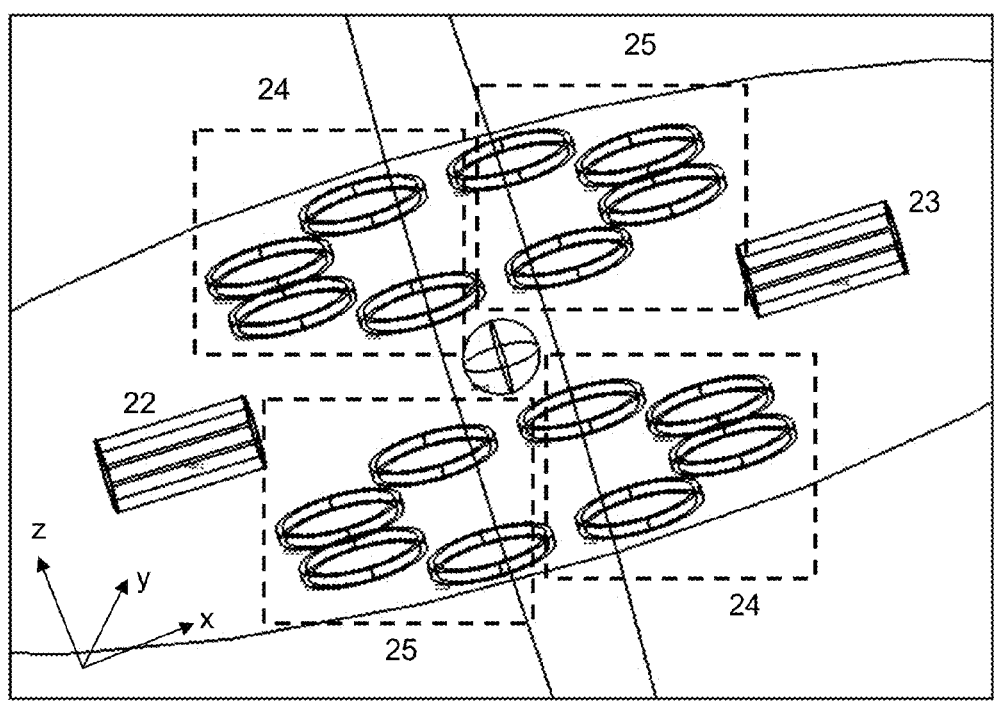
FIG. 5 shows an isometric view of the MRI arrangement of FIG. 4.

In an example of the present disclosure, eight Maxwell-like coils in two sets of four may be employed in an MRI arrangement suitable for use with radiotherapy, as shown in FIGS. 4 and 5. The coils in each set may be arranged so that their collective shape may be similar to a banana-shaped coil since the coils may fit inside a banana-shaped outline. Circular coils have been used in this example rather than banana-shaped coils because circular coils are simpler to model and construct than banana-shaped coils. Banana-shaped coils typically require complex construction methods and may be more difficult to model. However, any suitable coil shapes may be used.

FIG. 4 shows the top plane of an example coil arrangement and the current directions in individual coils. FIG. 5 shows a three dimensional view. For each plane, the coils may be separated in to two sets, 4 that are located in the region where x is less than zero, and four that are in the region where x is greater than zero. In the example shown, the centre of the coil arrangement may define the origin (i.e., x=y=z=0), with the eight Maxwell-like coils arranged with the upper and lower coils of each Maxwell-like coil in two parallel x-y planes (e.g., at z=50 and −50 cm). In this example, the radius of each individual coil may be about 50 cm; the centers of the individual coils may be about 81 cm from the z-axis, with angular separation at approximately $\pi/4$. In the top plane shown in FIG. 4, the four coils 24 in one set may have, for example, clockwise current flow, whereas the four other coils 25 in the other set may have, for example, counterclockwise current flow. In the bottom plane as shown in FIG. 5, the direction of current flow may be inverted so that coils with counterclockwise current flow 25 may be directly under the coils in the upper plane that have clockwise current flow 24 and coils with clockwise current flow 24 may be directly below coils that have counterclockwise flow 25. This configuration may produce a transverse magnetic field in the z=0 plane that may be directed in the positive x-direction. The transverse magnetic field of the four sets of Maxwell-like coils for x>0 may become additive with the transverse magnetic field for the Maxwell-like coils in the region where x<0; the result may be a region of magnetic field homogeneity or near homogeneity at the geometric center of the arrangement. Those skilled in the art will recognize that a multitude of coils arrangements, including non-circular coils, can produce a similar magnetic field arrangement. Although the coils have been described with example coordinate locations in space, this may be varied, as described above.

The magnetic field in this example, when plotted along the x-axis, may show a field reversal. In order to generate a zone of magnetic field suitable for a linear accelerator outside of the magnet, two additional focusing magnets may be added. The focusing magnets (in this example, solenoid magnets) may generate a suitable focusing magnetic field in the area where the linear accelerator may be located. These focusing magnets may be located on the x-axis, with current distributions such that the magnetic field may be also in the positive x-direction. These focusing magnets may also be referred to as linear accelerator focusing magnets. Those skilled in the art will recognize that these linear accelerator focusing magnets can be positioned in many location along the x-axis of the arrangement (e.g., at about 80 cm from the centre of the coil arrangement), with many different current densities, including non-uniform current densities. These focusing magnets may generate a positively directed magnetic field that may be in the same direction as the magnetic field in the central region (i.e., the imaging area) of the MRI. Although a pair of focusing magnets may be used, to help maintain symmetry and help preserve homogeneity of the magnetic field in the imaging area, it may also be possible to use only one focusing magnet. The use of only one focusing magnet, which may provide a focusing magnetic field only on one side of the coil arrangement, may give rise to a less homogeneous magnetic field in the imaging area. This may be corrected or compensated using conventional magnet optimization techniques. In some applications, such a decrease in homogeneity may be acceptable, and the use of only one focusing magnet may provide a decrease in cost. In some examples, more than two focusing magnets may be used, as appropriate.

In the region where the linear accelerator focusing magnets are located, a linear accelerator can be positioned, in the peripheral area of the coils, such that the electron motion within it may be focused by the external magnetic field. The linear accelerator may be positioned such that the radiation treatment beam emitted may be directed into the imaging area and may be substantially parallel to the transverse direction of the magnetic field in the imaging area. The linear accelerator may also be substantially centered on the imaging area. The linear accelerator may be substantially parallel to the transverse magnetic field. Typically, the linear accelerator may be centered on an isocentre for the radiotherapy treatment, for example within an accuracy of less than 1 mm. The treatment isocentre may be the same as the magnet or imaging isocentre (e.g., for simplicity of calculation) or may be different (e.g., in a different transverse plane).

Figure 6:
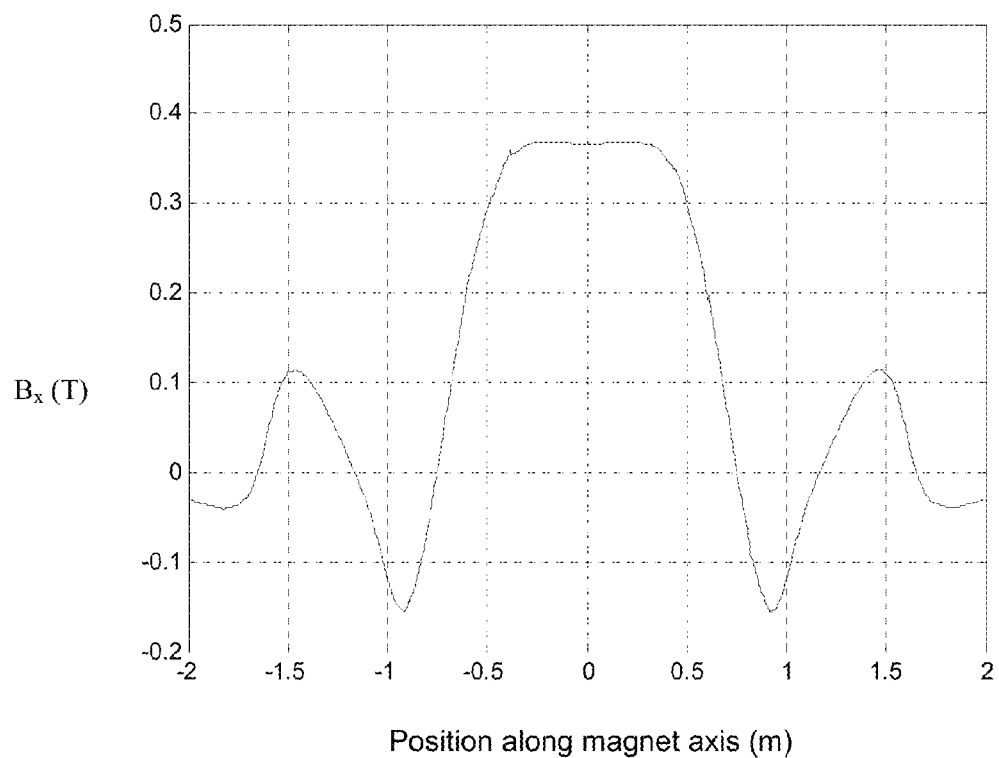
FIG. 6 shows an example of the magnetic field along the x-axis of the MRI arrangement of FIG. 4.

With the linear accelerator focusing magnets added to the coil arrangement, a magnetic field pattern may be generated such as that shown in FIG. 6. In this example, the individual coils may have a current density of about $1\times10^9$ A/m$^2$ each, and the focusing magnets (in this example, solenoid cylinders) may have a current density of about $5\times10^3$ A/m$^2$ each. Those skilled in the art will recognize that these current densities are not unique, and that many other current densities can be utilized to achieve the same purpose.

An imaging target (e.g., human patient, imaging phantom, animal model, etc.) may be placed in the imaging area for both MRI and for radiotherapy. For example, a human patient may be positioned in the imaging area along the z-axis. The MRI apparatus may be configured to accommodate a human patient as the imaging target. For example, each Maxwell-like coil may have a distance between the individual coils sufficient to accommodate the upper half of a human (e.g., head and torso), for example the individual coils may be spaced apart about 100 cm. The focusing magnets may be positioned a similar distance from the magnetic isocentre, for example about 105 cm from the centre of the patient. In an example arrangement, the Maxwell-like coils may each have a radius of about 25 cm, and may be arranged to provide a space sufficient to accommodate the patient, for example a space of about 112 cm diameter, and the coils may each have a current density of about $10^9$ A/m$^2$. The focusing magnets may each have a current density of about $5\times10^6$ A/m$^2$. Such a configuration may generate a relatively homogeneous magnetic field in the imaging area, which may have a value of about 0.36 T, with a focusing field of about 0.1 T located about 116 cm from the magnetic isocentre, for example. Other configurations may be possible, and may be varied depending on the application and/or the imaging target, for example to achieve different field strengths and/or positions.

FIG. 6 shows an example magnetic field on the z=0 plane. In this plot, a positive value indicates a magnetic field in the same direction as the transverse magnetic field in the imaging area, and a negative value indicates a magnetic field in an opposite direction to the transverse magnetic field in the imaging area. The magnetic field reverses direction when outside the ring of Maxwell-like coils, but a region of positive magnetic field is generated at a position suitable for a linear accelerator by placing a focusing magnet (e.g., a solenoid magnet) along the x-axis, but displaced away from the magnet isocentre. To preserve symmetry, an optional second solenoid magnet with identical current distribution may be placed on the opposite side. The linear accelerator may be positioned in the peripheral area having a positive magnetic field (i.e., the magnetic field generated by the focusing magnet, in the same direction as the magnetic field in the imaging area). An opposing magnetic field is generated in between this region and the imaging region of the MRI magnet.

A feature of the magnetic field, for example as shown in FIG. 6, may be the presence of a null magnetic field at a distance from the magnet isocentre, in the peripheral area (in this example, at approximately 116 cm from the magnet isocentre). Another null may exist at a distance from the magnet isocentre but within the imaging area (in this example, at about 73 cm from the isocentre leaving approximately 43 cm of opposing magnetic field in between). In this example, the peak value of the null area is approximately −0.15 T. If the imaging target were placed at 116 cm from the magnet isocentre, the entire collimation system could be placed in a region of negative magnetic field so that contamination electrons may be defocused away from the patient's surface. This may help to reduce or eliminate the surface dose on the patient due to these scattered electrons, thus promoting the clinical utility of the linear accelerator-MRI combination. Those skilled in the art will recognize that other magnetic field arrangements are possible, with negative magnetic field (also referred to as field reversal) at different physical locations. Further, those skilled in the art will recognize that different magnetic field strengths could be utilized, and be generated from different (e.g., non-circular) coil arrangements or circular coils that have different current densities in them. These other coil arrangements can achieve the same desired effect where a magnetic field reversal is generated in a region where photons are traversing a region in between a linear accelerator and a patient in an integrated linear accelerator-MRI system.

Figure 7A:
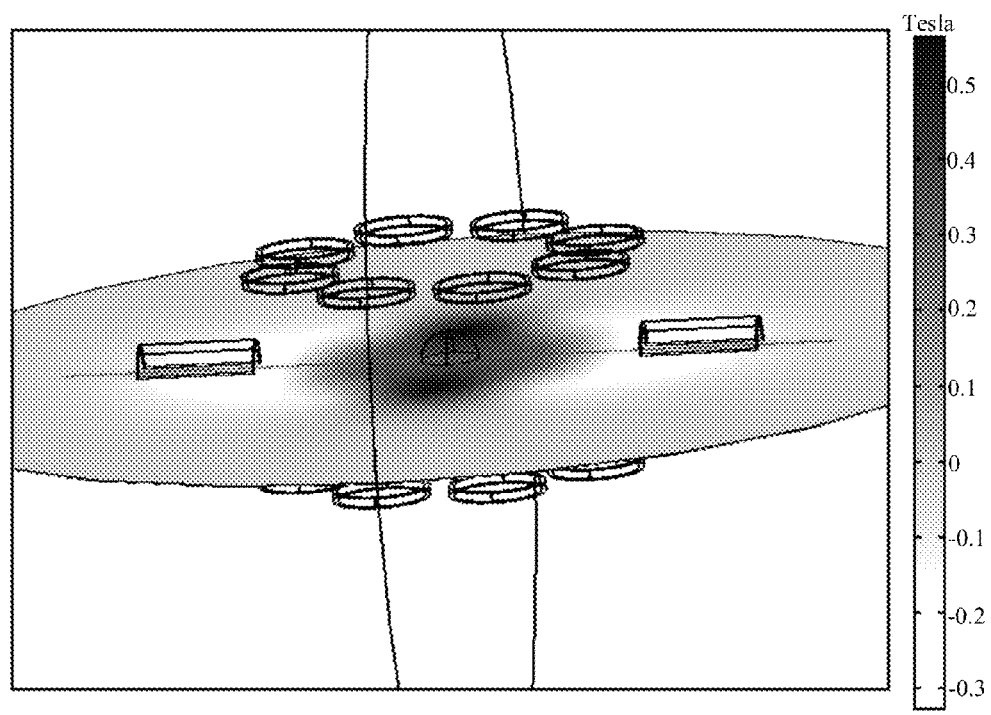
FIG. 7A shows an isometric view of an example transverse magnetic field produced by the MRI arrangement of FIG. 4.
Figure 7B:
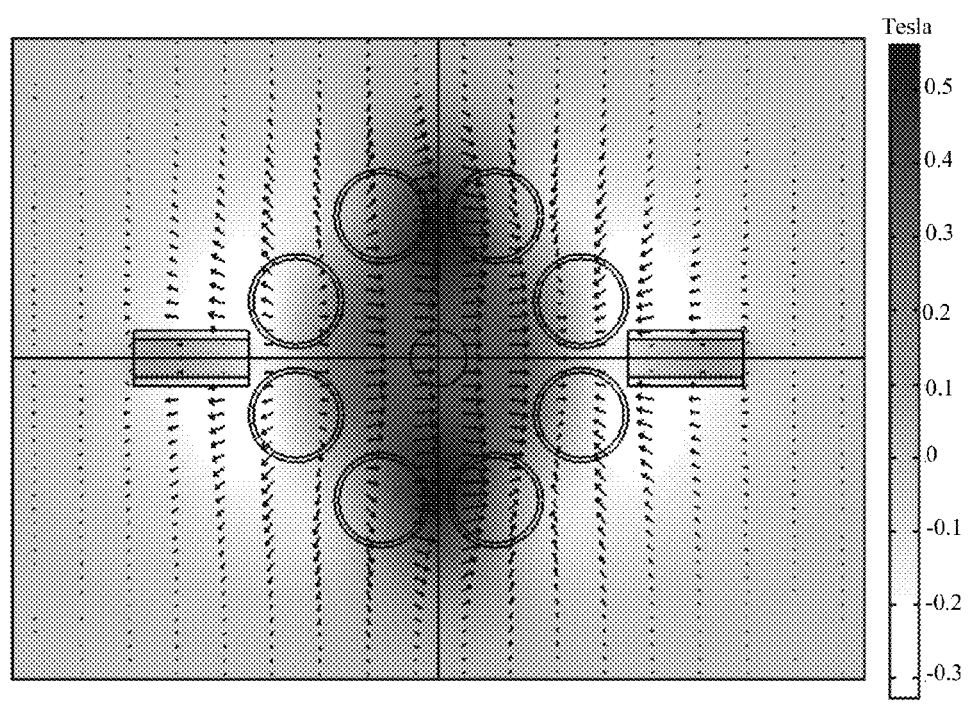
FIG. 7B shows a view of the transverse plane of the magnetic field of FIG. 7A.

An example of the generated three dimensional magnetic field pattern is shown in FIGS. 7A and 7B. FIG. 7A shows a three dimensional view of the example coil assembly and the example transverse field generated, while FIG. 7B shows a view of the transverse plane specifically with magnetic field directions indicated. This magnetic field pattern may be further optimized or improved for imaging by MRI, for example using conventional optimization techniques[33] and can be used to optimize or improve the currents or placement of the coils, for example those shown in FIGS. 4 and 5, such that imaging by MRI may be feasible or improved. In the example shown, the fringe field of the magnet assembly and resulting field pattern, for example as shown in FIGS. 7A and 7B, may extend a significant distance from the magnet centre, which may be undesirable in MRI. Magnet shielding techniques are also well known, and those skilled in the art will recognize that a similar shielded magnet assembly with appropriate shielding can be designed within the scope of the present disclosure. Other such conventional variations to the MRI apparatus may also be carried out within the scope of the present disclosure.

The effectiveness of the magnetic field pattern in removing the undesired surface dose that was described by Litzenberg and colleagues[32] can be evaluated using various dose calculation and particle tracking techniques, such as those described by Chen and colleagues[34]. These methods utilize various computer codes that employ industry standard Monte Carlo methods that can track photon and charged particle trajectories, and evaluate dose deposition of these particles in a uniform or non-uniform magnetic field[35,36].

Variations

Figure 8A:
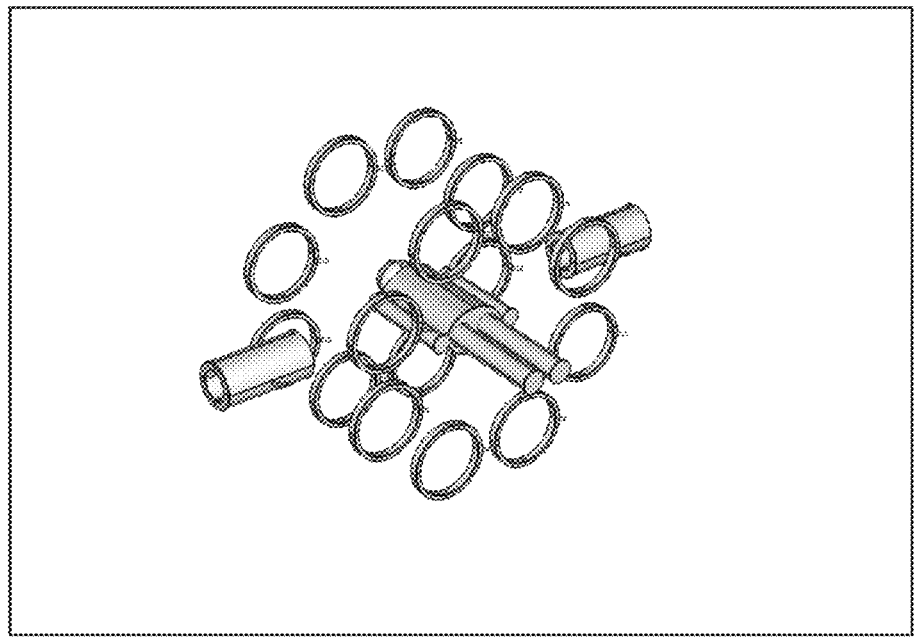
FIGS. 8A-8E illustrate an example MRI arrangement suitable for use in rotational radiotherapy.
Figure 8B:
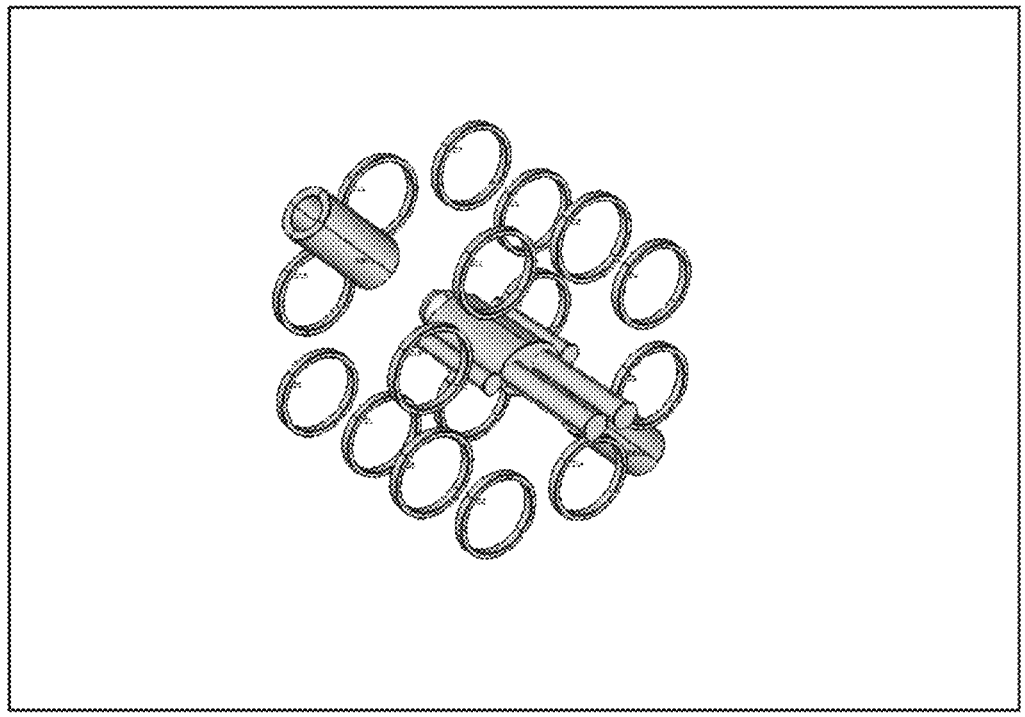
Figure 8C:
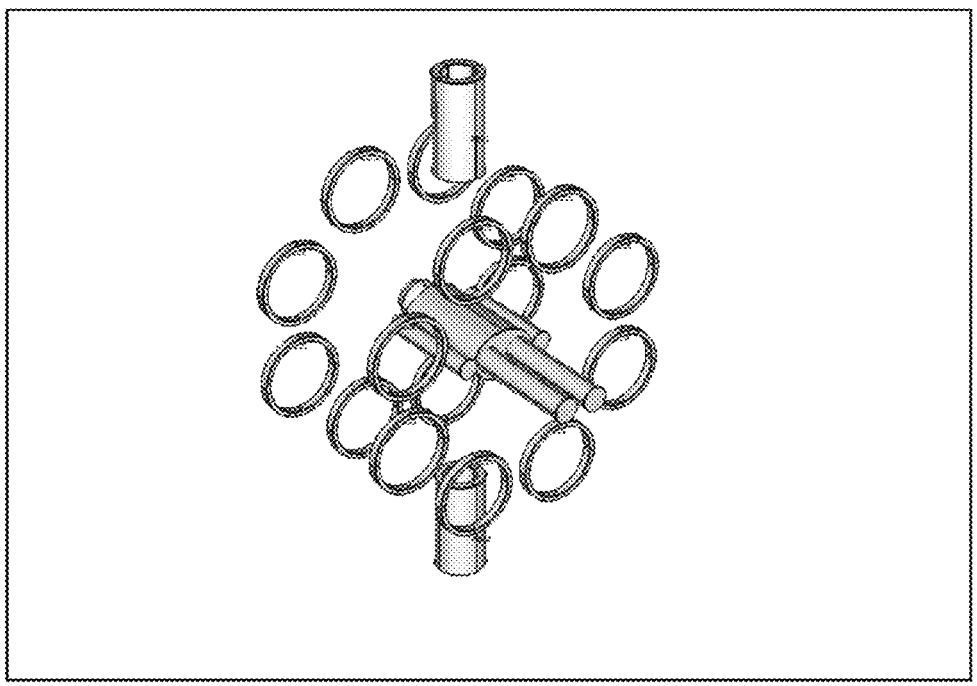
Figure 8D:
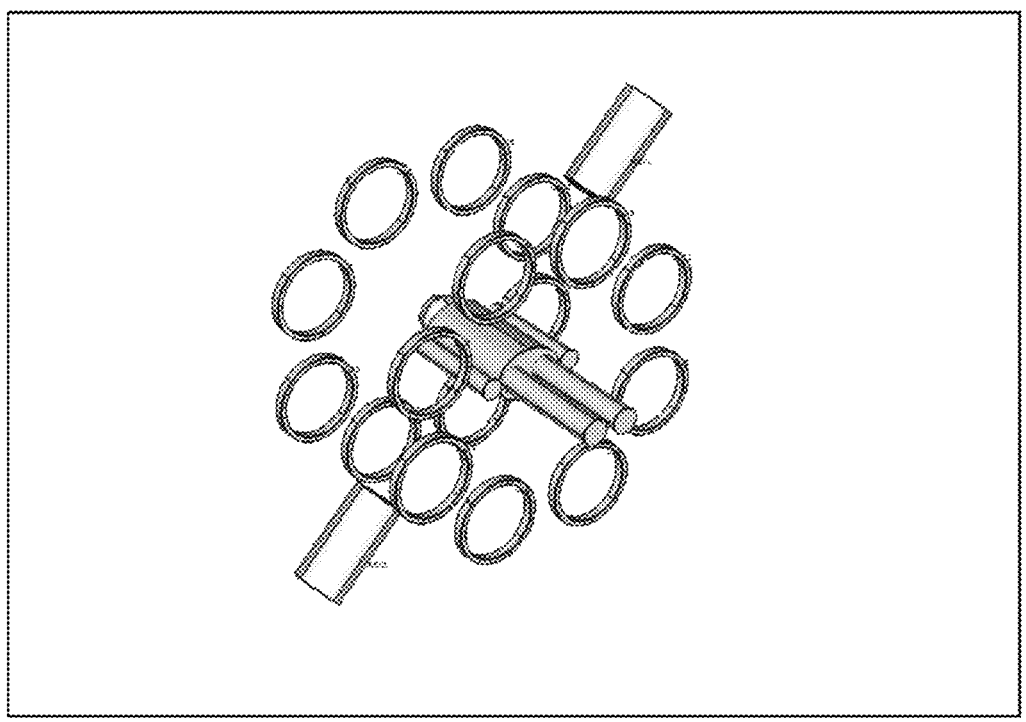
Figure 8E:
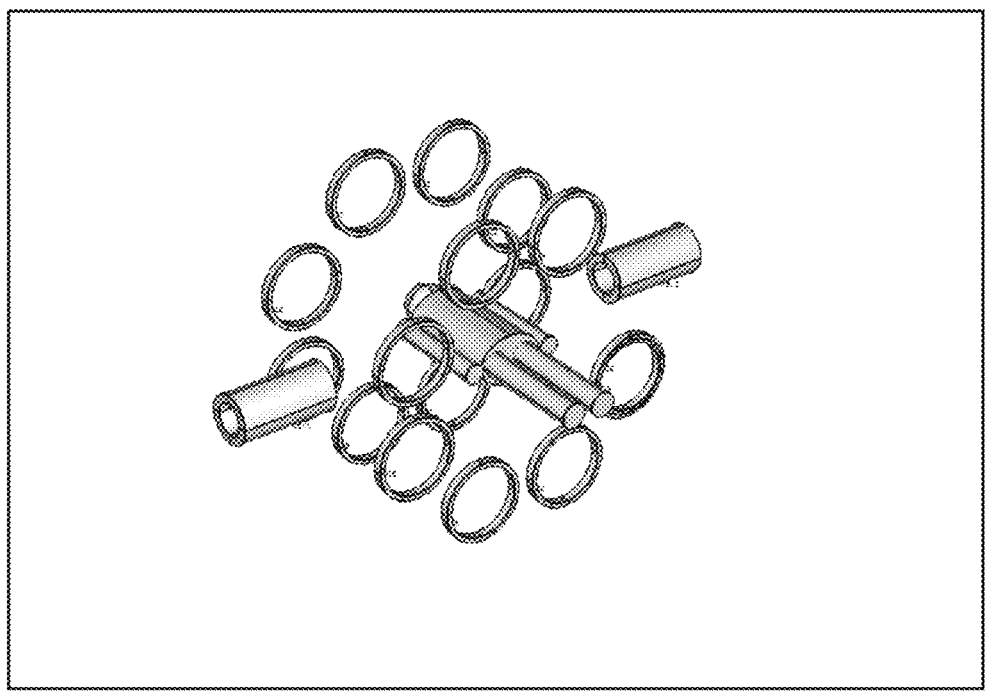

For use in radiotherapy, in some applications the linear accelerator (linac) may be rotated about the patient (e.g., in rotational radiotherapy). For an example magnet configuration, an example of such rotation about an imaging target (a human patient positioned along the z-axis in this example) is shown in FIGS. 8A to 8E. In FIGS. 8A to 8E, three dimensional view of different example MRI-linac coil configurations are shown at different gantry angles. In FIG. 8A, gantry=−90°; in FIG. 8B, gantry=−45°; in FIG. 8C, gantry=0°; in FIG. 8D, gantry=45°; and in FIG. 8E, gantry=90°. In this example, the magnet may be approximately cylindrically symmetrical about the z-axis, and so the imaging target may be placed along this axis. This orientation may leave a relatively large clearance about the target, and so it may be suitable for radiotherapy, where the patient may be in positions that require a relatively large bore imaging device (such as in breast tangents, where one arm is elevated and the other not).

The example embodiment described above may be one where the magnet may be oriented such that the z-axis (e.g., as indicated in FIG. 5) is relatively horizontal with respect to the imaging target. For imaging a human patient, the patient may thus be positioned such that the caudal-cranial direction may be parallel to the z-axis in such an arrangement.

In this example embodiment, it may be necessary to rotate the entire arrangement, including the Maxwell-like coils with the linac during rotational therapy. In an example where the Maxwell-like coils are superconducting, movement of the Maxwell-like coils may be possible, but may require special techniques to prevent failure of the magnet, such as quenching. As well, it may be necessary to maintain the speed of the movement within certain limits.

Figure 9:
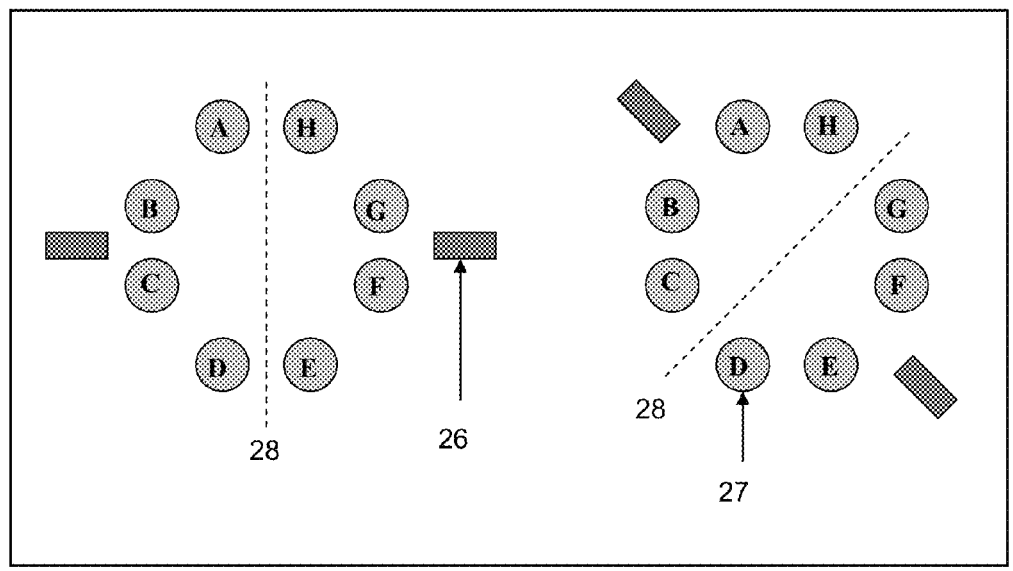
FIG. 9 shows another example MRI arrangement suitable for use with rotational radiotherapy.

Another example embodiment is shown in FIG. 9, which may be useful for removing the need for rotation of the entire arrangement. FIG. 9 shows an example of how a variable direction magnetic field can be generated without movement of the Maxwell-like coils. This may be accomplished, for example, by changing the plane of symmetry of the Maxwell-like coil arrangement. This may be useful, for example, for a resistive magnet arrangement. The currents (i.e., polarities) in each of the Maxwell-like coils can be changed so that the plane of symmetry with respect to the Maxwell-like coils can be rotated without moving the MRI coil assembly 27. This may be suitable where the Maxwell-like coils have similar geometries and configurations. Specifically, the individual Maxwell-like coils in each of the two opposing sets may be shifted. For example, in a top-view, in the left figure, coils A, B, C and D may be in one set of coils (e.g., with clockwise currents) while coils E, F, G and H may be in the second set of coils (e.g., with counter-clockwise currents), with the focusing magnets positioned at 90° gantry giving rise to an plane of symmetry at 0°, such that the linear accelerator may be positioned at 90° gantry. In the right figure, the polarities of coils H and D may be changed such that now coils H, A, B and C are in one set of coils (e.g., with clockwise currents) while coils D, E, F and G are in the other set of coils (e.g., with counter-clockwise currents), with the focusing magnets positioned at −45° gantry, giving rise to an plane of symmetry at 45° such that the linear accelerator may be positioned at −45° gantry. In general, the rotation of the plane of symmetry 28 may match or correspond to the rotation of the linear accelerator 26.

This ability to change the polarities of individual coils, which may remove the need for magnet rotation, may be an advantage of using a two sets of Maxwell-like coils rather than a single pair of banana-shaped coils. A person skilled in the art would understand that the number of individual coils in this example Maxwell-like coil arrangement may be increased or decreased as desired, for example a greater number of individual coils may provide for finer rotation angles in rotation radiotherapy.

This technique may be suitable for MRI techniques that employ polarizing fields, such as field cycling MRI.

In general, the disclosed MRI arrangement may avoid interfering with the operation of the linear accelerator since the magnetic field may be generated such that it may be parallel to the direction of electron motion, and thus may act as a focusing (in the case of desired X-ray treatment beam) or defocusing (in the case of undesired stray electrons) field.

The linear accelerator may thus have relatively simple geometrical access to the imaging region.

There may be little or no distortion to the dose distribution on the patient since the magnetic field may be substantially parallel to the direction of photon travel. Thus, scattered electrons in the patient may also tend to be parallel to the magnetic field. These may then be focused instead of pushed into a curved trajectory, as in the case where the magnetic field is perpendicular to the photon direction.

A reverse magnetic field may be generated in the region in between the linac target and the patient. Thus, the beam collimation system and a region slightly distal to it may be immersed in a reverse magnetic field that may defocus scattered electrons. This may reduce or eliminate electron contamination of the photon beam and thus may reduce or eliminate the surface dose and may produce a clinically useful radiation beam.

The presently disclosure apparatus and system may be useful for integration of MRI and radiotherapy. For example, the disclosed apparatus may provide for an axial magnetic field. The disclosed apparatus may avoid or reduce the need to magnetically decouple the linear accelerator. The disclosed apparatus may also reduce or eliminate any surface dose effects. The geometry of the disclosed apparatus may not be constricting, for example there may be space for adding other imaging or therapy components, such as, for example, cryogenics, mechanical supports, gradient coils and/or RF coils.

The embodiments of the present disclosure described above are intended to be examples only. Alterations, modifications and variations to the disclosure may be made without departing from the intended scope of the present disclosure. In particular, selected features from one or more of the above-described embodiments may be combined to create alternative embodiments not explicitly described. All values and sub-ranges within disclosed ranges are also disclosed. The subject matter described herein intends to cover and embrace all suitable changes in technology. All references mentioned are hereby incorporated by reference in their entirety.

REFERENCES

1. Hammer B. E., Christensen, N. L., King, W., Conroy, M. J., Pogue, N. Integration of a 6 MeV Electron Beam LINAC with a 1.5 T MRI Scanner. In: Proc Intl Soc Mag Reson Med 2004; 2004. p. 972
2. Fallone B. G., Murray B., Rathee S., et al. "First MR images obtained during megavoltage photon irradiation from a prototype integrated linac-MR system," Med Phys, 36, 2009, 2084-8
3. Raaymakers B. W., Lagendijk J. J., Overweg J., et al. "Integrating a 1.5 T MRI scanner with a 6 MV accelerator: proof of concept," Phys Med Biol, 54, 2009, N229-37
4. Bielajew A. F. "The effect of strong longitudinal magnetic fields on dose deposition from electron and photon beams," Med Phys, 20, 1993, 1171-9
5. Kirkby C., Stanescu T., Rathee S., Carlone M., Murray B., Fallone B. G. "Patient dosimetry for hybrid MRI-radiotherapy systems," Med Phys, 35, 2008, 1019-27
6. Nath R., Schulz R. J. "Modification of electron-beam dose distributions by transverse magnetic fields," Med Phys, 5, 1978, 226-30
7. Paliwal B. R., Wiley A. L., Jr., Wessels B. W., Choi M. C. "Magnetic field modification of electron-beam dose distributions in inhomogeneous media," Med Phys, 5, 1978, 404-8
8. Raaijmakers A. J., Hardemark B., Raaymakers B. W., Raaijmakers C. P., Lagendijk J. J. "Dose optimization for the MRI-accelerator: IMRT in the presence of a magnetic field," Phys Med Biol, 52, 2007, 7045-54
9. Raaijmakers A. J., Raaymakers B. W., Lagendijk J. J. "Integrating a MRI scanner with a 6 MV radiotherapy accelerator: dose increase at tissue-air interfaces in a lateral magnetic field due to returning electrons," Phys Med Biol, 50, 2005, 1363-76
10. Raaijmakers A. J., Raaymakers B. W., Lagendijk J. J. "Experimental verification of magnetic field dose effects for the MRI-accelerator," Phys Med Biol, 52, 2007, 4283-91
11. Raaijmakers A. J., Raaymakers B. W., Lagendijk J. J. "Magnetic-field-induced dose effects in MR-guided radiotherapy systems: dependence on the magnetic field strength," Phys Med Biol, 53, 2008, 909-23
12. Raaijmakers A. J., Raaymakers B. W., van der Meer S., Lagendijk J. J. "Integrating a MRI scanner with a 6 MV radiotherapy accelerator: impact of the surface orientation on the entrance and exit dose due to the transverse magnetic field," Phys Med Biol, 52, 2007, 929-39
13. Raaymakers B. W., Raaijmakers A. J., Kotte A. N., Jette D., Lagendijk J. J. "Integrating a MRI scanner with a 6 MV radiotherapy accelerator: dose deposition in a transverse magnetic field," Phys Med Biol, 49, 2004, 4109-18
14. Weinhous M. S., Nath R., Schulz R. J. "Enhancement of electron beam dose distributions by longitudinal magnetic fields: Monte Carlo simulations and magnet system optimization," Med Phys, 12, 1985, 598-603
15. Whitmire D. P., Bernard D. L., Peterson M. D., Purdy J. A. "Magnetic enhancement of electron dose distribution in a phantom," Med Phys, 4, 1977, 127-31
16. Burke B., Lamey M., Rathee S., Murray B., Fallone B. G. "Radio frequency noise from clinical linear accelerators," Phys Med Biol, 54, 2009, 2483-92
17. Lamey M., Rathee, S., Johnson, L., Carlone, M., Blosser, E., Fallone, B. G. Radio frequency noise from the modulator of a linac. In: IEEE Transactions on Electromagnetic Compatibility; 2010.
18. Lamey M., Burke B., Blosser E., Rathee S., De Zanche N., Fallone B. G. "Radio frequency shielding for a linac-MRI system," Phys Med Biol, 55, 2009, 995-1006
19. Lamey M., Yun J., Burke B., Rathee S., Fallone B. G. "Radio frequency noise from an MLC: a feasibility study of the use of an MLC for linac-MR systems," Phys Med Biol, 55, 2009, 981-94

20. Amies C. J., Beasley, P., Celi, J. C., Held, O., Hernandez-Guerra, F. M., Kruip, M. J. M., Vester, M., Combined Radiation Therapy and Magnetic Resonance Unit, US2008/0208036 A1, 2008
21. Dempsey J. F., System for delivering conformal radiation while simultaneously imaging soft tissue, US 2005/0197564 A1, 2005
22. Fallone B. G., Carlone, M. C, Murray, B, Integrated External Beam Radiotherapy and MRI System, 2009/0149735 A1, 2009
23. Green M. S., Radiotherapy Machine Including Magnetic Resonance Imaging System, U.S. Pat. No. 6,366,798 B2, 2002
24. Kornblau G., Neustadter, D. M., Stokar, S., Combination MRI and Radiotherapy System and Methods of Use, WO 2009/113069 A1, 2009
25. Lagendijk J., MRI in guided radiotherapy apparatus with beam heterogeneity compensators, WO 2004/024235 A1, 2004
26. Carlone M., Fallone, B. G., Murray, B., Radiation Therapy System, WO 2009/155700 A1, 2010
27. Schenck J. F., Jolesz F. A., Roemer P. B., et al. "Superconducting open-configuration MR imaging system for image-guided therapy," Radiology, 195, 1995, 805-14
28. Septier A. L. Focusing of Charged Particles: Academic Press; 1967
29. Septier A. L. Applied charged particle optics. New York: Academic Press; 1980
30. Humphries S. Principles of charged particle acceleration. New York: J. Wiley; 1986
31. Karzmark C. J., Nunan C. S., Tanabe E. Medical electron accelerators. New York: McGraw-Hill, Inc., Health Professions Division; 1993
32. Litzenberg D. W., Fraass B. A., McShan D. L., et al. "An apparatus for applying strong longitudinal magnetic fields to clinical photon and electron beams," Phys Med Biol, 46, 2001, N105-15
33. Romeo F., Hoult D. I. "Magnet field profiling: analysis and correcting coil design," Magn Reson Med, 1, 1984, 44-65
34. Chen Y., Bielajew A. F., Litzenberg D. W., Moran J. M., Becchetti F. D. "Magnetic confinement of electron and photon radiotherapy dose: a Monte Carlo simulation with a nonuniform longitudinal magnetic field," Med Phys, 32, 2005, 3810-8
35. Kawrakow I., Rogers, D. W. O. The EGSnrc Code System: Monte Carlo Simulation of Electron and Photon Transport. Ottawa: NRC; 2003. Report No.: NRCC Report PIRS-701.
36. Salvat F., Fernández-Varea, J. M., Acosta, Sempau, J. PENELOPE: A Code System for Monte Carlo Simulation of Electron and Photon Transport. Issy-les-Moulineaux: OECD Nuclear Energy Agency; 2003.
37. Kruip M. J. M., Beasley, P., Superconducting open MRI magnet with Transverse Magnetic Field, US 2004/0085170 A1, 2004
38. KRUIP M. J. M., BEASLEY, Paul, Particle radiation therapy equipment comprising magnetic resonance imaging means, WO 2006/136865 A1, 2006

The invention claimed is:

1. A magnetic resonance imaging (MRI) apparatus suitable for radiotherapy, the apparatus comprising:
    two sets of coil pairs, each set having at least one coil pair, each coil pair comprising two individual coils having different polarities, superimposed over each other and sharing a common axis of rotation;
    the coil pairs in each set of coil pairs sharing a common transverse plane;
    the two sets of coil pairs sharing the common transverse plane and being parallel to and spaced apart from each other, the two sets of coil pairs having opposing polarities, and defining a common plane of symmetry and an imaging area between the two sets of coil pairs;
    the two sets of coil pairs being configured to generate a substantially homogenous electromagnetic field in a first transverse direction in the common transverse plane, in the imaging area between the two sets of coil pairs;
    the two sets of coil pairs also being configured to generate peripheral electromagnetic fields in a second transverse direction opposite to the first transverse direction in a peripheral area outside of the imaging area; and
    at least one focusing magnet positioned in the peripheral areas, substantially parallel to the first transverse direction, the at least one focusing magnet being configured to generate a focusing electromagnetic field in a focusing area, in a direction substantially the same as the first transverse direction;
    wherein at least a portion of the peripheral electromagnetic fields is maintained in a defocusing area between the focusing area and the imaging area.

2. The apparatus of claim 1, wherein there are two focusing magnets, on opposing sides of the two sets of coil pairs, symmetrically on either side of the plane of symmetry.

3. The apparatus of claim 1, wherein the individual coils of the coil pairs are circular coils having equal radii.

4. The apparatus of claim 1, wherein each set of coil pairs comprises four coil pairs arranged in an arc-like configuration.

5. The apparatus of claim 1, wherein the at least one focusing magnet is a solenoid magnet.

6. The apparatus of claim 1, wherein the two sets of coil pairs are sized and positioned to define the imaging area suitable to accommodate a human patient.

7. The apparatus of claim 1, wherein the apparatus is rotatable about the imaging area.

8. The apparatus of claim 1, wherein each set of coil pairs comprise a plurality of coil pairs, wherein the polarity of each coil pair is individually selectable to dynamically define the plane of symmetry in any one of a plurality of defined orientations and to dynamically change the orientation of the transverse directions of the generated electromagnetic fields, and wherein the at least one focusing magnet is rotatable about the imaging area to match the changed transverse directions.

9. The apparatus of claim 1, wherein the apparatus is configured to accommodate a linear accelerator for radiotherapy in the focusing area, where the linear accelerator is configured to emit a radiation beam in the direction of the first transverse direction.

10. The apparatus of claim 9 wherein a dose distribution generated by the linear accelerator is undisturbed by the generated electromagnetic fields.

11. A system for magnetic resonance imaging (MRI) suitable for use with radiotherapy, the system comprising:
    the apparatus of claim 1; and
    a linear accelerator for radiotherapy, the linear accelerator being positioned to emit a radiation beam into the imaging area, in the direction of the first transverse direction, the linear accelerator also being positioned in the focusing area.

12. The system of claim 11, wherein the apparatus comprises two focusing magnets, on opposing sides of the two sets of coil pairs, symmetrically on either side of the plane of symmetry.

13. The system of claim 11, wherein, in the apparatus, the individual coils of the coil pairs are circular coils having equal radii.

14. The system of claim 11, wherein, in the apparatus, each set of coil pairs comprises four coil pairs arranged in an arc-like configuration.

15. The system of claim 11, wherein, in the apparatus, the at least one focusing magnet is a solenoid magnet.

16. The system of claim 11, wherein, in the apparatus, the two sets of coil pairs are sized and positioned to define the imaging area suitable to accommodate a human patient.

17. The system of claim 11, wherein the apparatus is rotatable about the imaging area.

18. The system of claim 11, wherein, in the apparatus, each set of coil pairs comprise a plurality of coil pairs, wherein the polarity of each coil pair is individually selectable to dynamically define the plane of symmetry in any one of a plurality of defined orientations and to dynamically change the orientation of the transverse directions of the generated electromagnetic fields, and wherein the at least one focusing magnet is rotatable about the imaging area to match the changed transverse directions.

19. The system of claim 11 wherein a dose distribution generated by the linear accelerator is undisturbed by the generated electromagnetic fields.

20. The system of claim 11 wherein the at least one focusing magnet of the apparatus is rotatable about the imaging area and the linear accelerator is also rotatable about the imaging area to match the focusing area of the focusing magnet.

* * * * *